United States Patent
Chen et al.

(10) Patent No.: US 10,054,519 B2
(45) Date of Patent: **\*Aug. 21, 2018**

(54) OSCILLATING MICROTOME WITH FLEXURE DRIVE

(71) Applicant: Tissuevision, Inc., Cambridge, MA (US)

(72) Inventors: Shih-Chi Chen, Shatin (HK); Martin L. Culpepper, Georgetown, MA (US)

(73) Assignee: TissueVision, Inc., Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/403,924

(22) Filed: Jan. 11, 2017

(65) Prior Publication Data

US 2017/0122844 A1    May 4, 2017

Related U.S. Application Data (63) Continuation of application No. 14/459,824, filed on Aug. 14, 2014, now Pat. No. 9,574,973, which is a continuation of application No. 13/166,472, filed on Jun. 22, 2011, now Pat. No. 8,839,700.

(60) Provisional application No. 61/357,896, filed on Jun. 23, 2010.

(51) Int. Cl.
| | |
|---|---|
| *B23D 7/06* | (2006.01) |
| *B26D 7/00* | (2006.01) |
| *G01N 1/06* | (2006.01) |
| *H04N 7/18* | (2006.01) |
| *G06T 7/00* | (2017.01) |

(52) U.S. Cl.
CPC .............. *G01N 1/06* (2013.01); *G06T 7/0002* (2013.01); *H04N 7/183* (2013.01); *G01N 2001/065* (2013.01)

(58) Field of Classification Search
CPC .............. G01N 1/06; G01N 2001/061; G01N 2001/065; Y10S 83/9155
USPC .......... 83/23, 915.5, 646, 697, 647, 25, 628; 267/181
See application file for complete search history.

(56) References Cited

U.S. PATENT DOCUMENTS

| | | | |
|---|---|---|---|
| 4,559,717 A | 12/1985 | Scire et al. | |
| 6,041,686 A | 3/2000 | Lihl et al. | |
| 6,651,538 B2 | 11/2003 | Tamura et al. | |
| 7,093,827 B2 | 8/2006 | Culpepper | |

(Continued)

FOREIGN PATENT DOCUMENTS

| | | |
|---|---|---|
| WO | WO 03093799 A1 | 11/2003 |
| WO | WO 2008030279 A2 | 3/2008 |

*Primary Examiner* — Omar Flores Sanchez
(74) *Attorney, Agent, or Firm* — Davis, Malm & D'Agostine, P.C.

(57) ABSTRACT

A microtome method and apparatus includes a microtome blade configured to oscillate in a direction transverse to a direction of advancing a cut, and a first flexure to support and guide the blade. The first flexure is compliant in the transverse direction while being stiff in the cut direction. A second flexure operatively engaged at one end portion with the first flexure, is stiff in the transverse direction while being compliant in the cut direction. The other end portion of the second flexure is rotatably engaged by an eccentric driven by a rotatable actuator, which oscillates the blade in the transverse direction while effectively isolating non-transverse motion from the blade. The second flexure is configured to move independently of any guides or other stationary objects during oscillation.

29 Claims, 9 Drawing Sheets

(56) References Cited

U.S. PATENT DOCUMENTS

| | | |
|---|---|---|
| 7,270,319 B2 | 9/2007 | Culpepper |
| 7,372,985 B2 | 5/2008 | So et al. |
| 2010/0000383 A1 | 1/2010 | Koos et al. |

OSCILLATING MICROTOME WITH FLEXURE DRIVE

This application is a Continuation of U.S. patent application Ser. No. 14/459,824, entitled Oscillating Microtome with Flexure Drive, filed on Aug. 14, 2014, which is a Continuation of U.S. patent application Ser. No. 13/166,472 (now U.S. Pat. No. 8,839,700), entitled Oscillating Microtome with Flexure Drive, filed on Jun. 22, 2011, which claims the benefit of U.S. Provisional Application Ser. No. 61/357,896, entitled Drive for an Oscillating Microtome, filed on Jun. 23, 2010.

BACKGROUND OF THE INVENTION (1) Field of the Invention

Embodiments of the present invention relates generally to a microtome having an oscillating blade. More particularly, this invention relates to a microtome having flexure drive in the form of a pair of compliant mechanisms having substantially orthogonal axes of predominant stiffness, configured to oscillate a blade transversely to a direction in which the cut advances.

(2) Background Information

A microtome is a sectioning instrument that allows for the cutting of thin slices of material known as sections. Microtomes are an important device in microscopy preparation, allowing for the preparation of sections for observation under transmitted light in optical microscopy, or in block face imaging, a microtome may be used to successively remove portions of the sample to expose the sample interior for imaging of the remaining specimen block. To section a sample, a blade similar to a razor blade is used which is drawn across the sample thus removing a thin slice of the specimen under consideration. Microtomes generally use steel, glass, or diamond blades depending upon the specimen being sliced and the desired thickness of the sections being cut. Steel blades are typically used to prepare sections of animal or plant tissues for light microscopy histology.

Oscillating blade microtomes are a variation of the basic microtome, and are widely recognized as superior for cutting thick sections from non-embedded or fresh tissue samples. The vibration amplitude, the vibrating speed, the angle of the blade, and the feed rate (of tissue samples) may all be controlled allowing for optimization of the cutting process. Fixed or fresh tissue pieces are typically embedded in low gelling-temperature agarose. The resulting agarose block containing the tissue piece is then glued to a stand and sectioned while submerged in a water or buffer bath.

Examples of conventional oscillating microtomes are disclosed in U.S. Pat. No. 6,651,538, entitled Microtome (the '538 patent), and U.S. Pat. No. 6,041,686, entitled Microtome Having an Oscillating Blade (the '686 patent). In the '538 patent, blade oscillation is provided by attaching the blade to a movable body that is coupled to a base by a resilient coupler. The base is provided with a driving electromagnet, and the movable body is provided with a permanent magnet. The movable body is then oscillated by supplying a control signal to the driving electromagnet. The '686 patent discloses an articulated connection coupled to an eccentric that converts the circular motion of an electric motor into an oscillating, substantially linear motion. These approaches each suffer from disadvantages associated with relatively imprecise oscillatory motion, including parasitic error motions, which tend to result in imprecise section thicknesses and tissue damage.

The '686 patent and similar motorized configurations may offer improved cutting accuracy relative to the directly-driven solenoid approaches of the '538 patent and the like. However, such motorized approaches suffer from disadvantages due to backlash inherent in the joint of the articulated arm. A joint is not perfectly stiff, and the magnitude of the backlash may be on the order of tens of microns to several hundred microns, introducing both higher order harmonics into the motion of the blade, and parasitic motion along orthogonal axes.

Drawbacks are also associated with the alternate approach disclosed in the '686 patent, of using a guide rail to guide the motion of a leaf spring connected to the blade assembly. In this alternate approach, as well as the articulated arm approach discussed above, the guide rail disadvantageously limits the upper frequency and magnitude of the oscillations due to friction between the oscillating spring/arm and the stationary rail. Furthermore, again due to backlash or imperfections of the guide rail, it is difficult, if not impossible, to eliminate unwanted motions perpendicular to the blade motion.

Another issue is potential buckling of the leaf spring. Any buckling would tend to reduce the stiffness along the desired direction of motion. Moreover, the friction from the guide rail generally leads to instrument wear and required maintenance.

There is therefore a need for an improved microtome that addresses the drawbacks of the prior art.

SUMMARY

In one embodiment of the present invention, a microtome apparatus includes a microtome blade configured to oscillate in a direction transverse to a direction of advancing a cut, and a first flexure configured to support and guide the blade, the first flexure configured to be compliant in the transverse direction while being stiff in the cut direction. A second flexure operatively engaged at one end portion with the first flexure, is configured for being stiff in the transverse direction while being compliant in the cut direction. The other end portion of the second flexure is rotatably engaged by an eccentric driven by a rotatable actuator, which oscillates the blade in the transverse direction while effectively isolating non-transverse motion from the blade. The second flexure is configured to move independently of any guides or other stationary objects during the oscillation.

In another aspect of the invention, a tissue scanning imaging apparatus includes the foregoing embodiment, an imaging device; and a stage configured to selectively advance a specimen sample into operative engagement with both the microtome apparatus and the imaging device.

Yet another aspect of the invention includes a method of treating a sample with the above-described microtome embodiment. This method includes oscillating the microtome blade in a direction transverse to a direction of advancing a cut, and moving the sample in the cut direction into operative engagement with the oscillating microtome blade to remove a section from the sample.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The present invention is illustrated by way of example and not limitation in the figures of the accompanying drawings, in which like references indicate similar elements and in which.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

Embodiments of the present invention are directed to microtomes which employ an oscillating blade to cut a specimen into sections. A primary flexure mechanism guides the motion of a blade, while being coupled to an oscillating actuator via a secondary flexure mechanism. The addition of a secondary flexure eliminates or significantly reduces unwanted mechanical coupling between the actuator and the first flexure, diminishing undesirable vibrations along directions nonparallel to the desired oscillatory blade motion. In particular, reduced vibrations in the out-of-plane direction (z-axis as shown and described herein) perpendicular to the surface of the specimen tend to reduce damage to the specimen during the cutting process. Moreover, the second flexure operates in a substantially frictionless manner, e.g., without the use friction-inducing guide rails.

Figure 2:
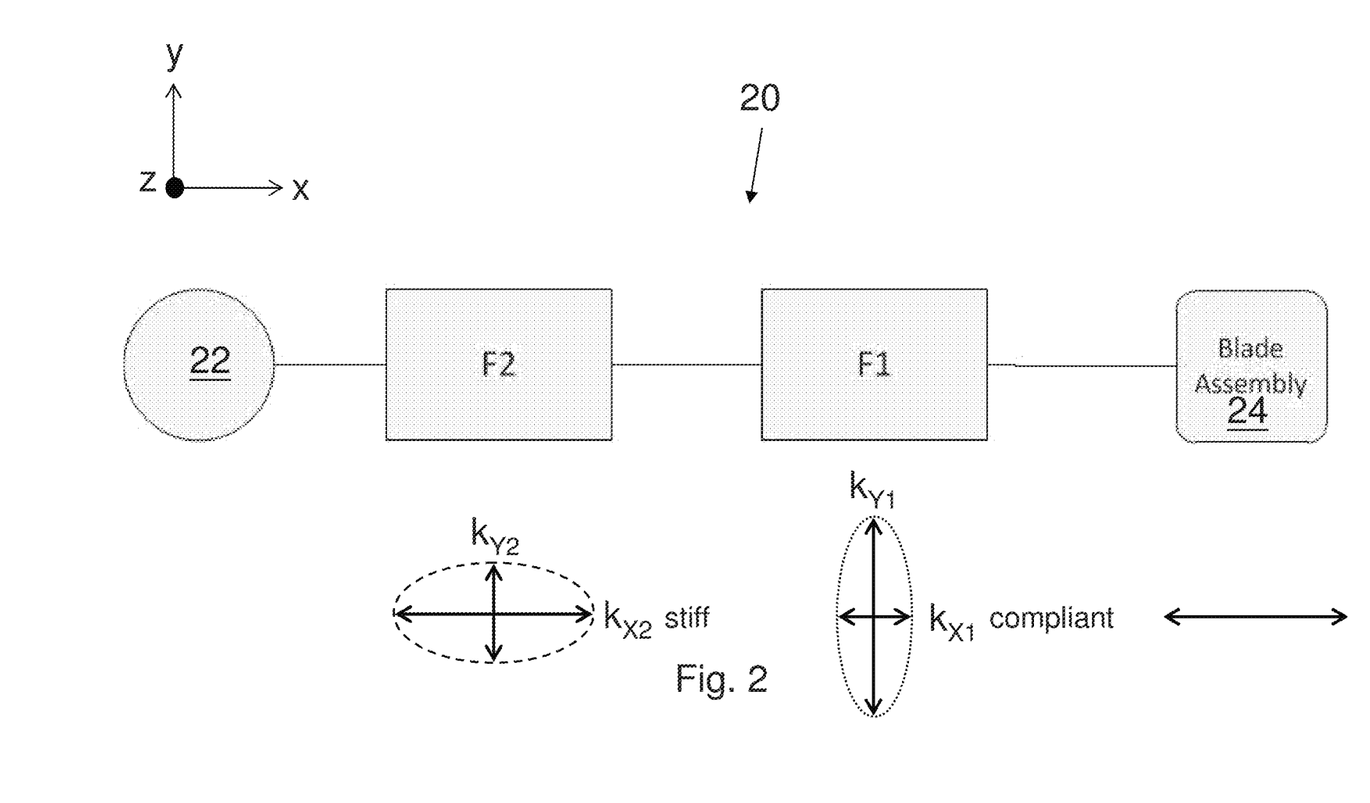
FIG. 2 is a block diagrammatic plan view of aspects of the present invention.
Figure 3A:
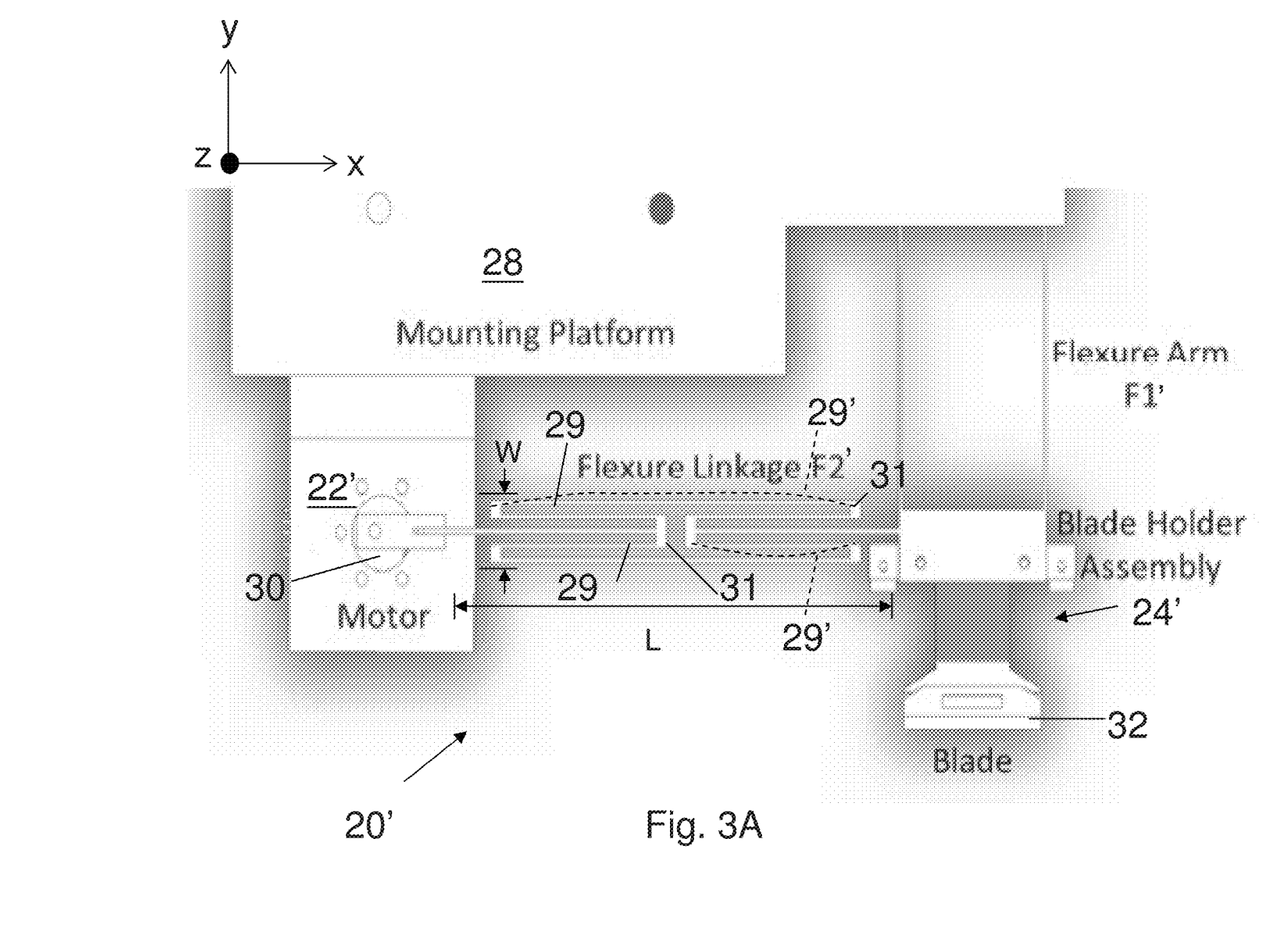
FIG. 3A is a schematic plan view of an embodiment of the present invention.
Figure 3B:
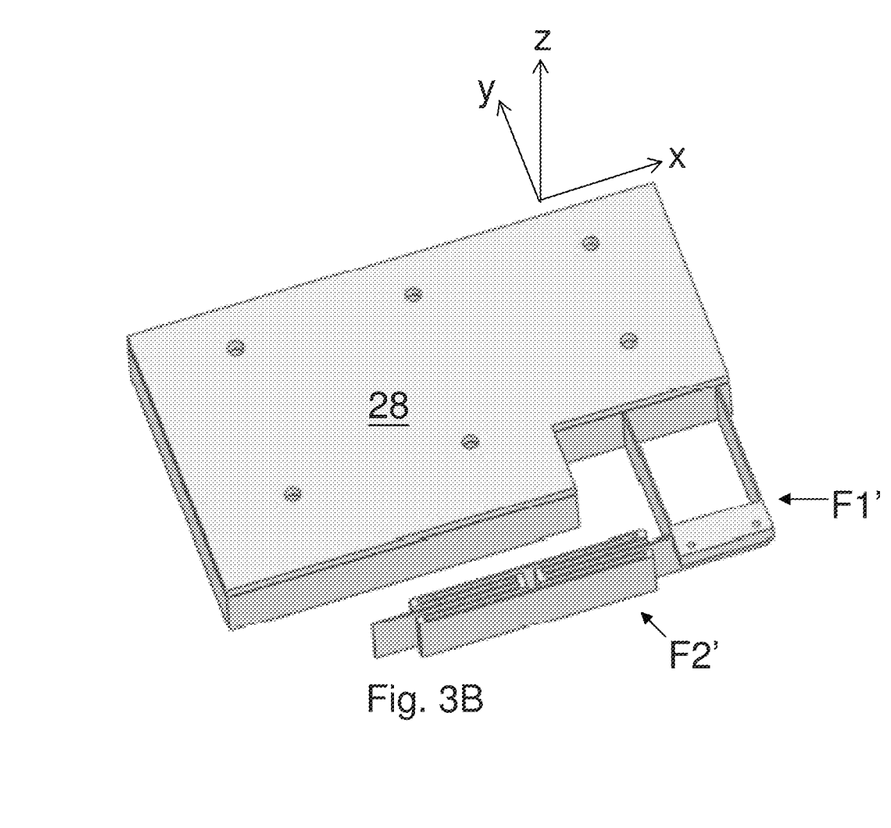
FIG. 3B is a perspective view of elements of the embodiment of FIG. 3.

In comparison to conventional oscillating microtome configurations, less waviness and damage to the section may be realized, allowing thinner sections and better quality imaging. This may be particularly useful for imaging sections and for block face imaging into the specimen block surface for microscope or other imaging investigations. Further advantages of this approach may include higher speed operation, better repeatability, lower cost, higher robustness, easier manufacturability, greater design flexibility, and longer instrument life, relative to conventional approaches.

Where used in this disclosure, the terms x, y or z "-axis" and/or "-direction" refer to one of three directions in the three dimensional orthogonal Cartesian coordinate system illustrated in FIGS. 2, 3A and 3B. The terms "cut direction" and/or "direction of advancing a cut" refer to the movement along the y-axis in the illustrated coordinate system. The term "transverse" refers to a direction other than substantially parallel to the cut direction, such as along the x-axis in the illustrated coordinate system.

An aspect of the present invention was the recognition that compliant mechanisms, also known as flexures, which have conventionally been used for controlled motion in very small increments (e.g., with translational resolution of nanometer increments, and rotational resolution of micro radians), may be successfully employed in the larger scale, high speed blade oscillation of microtomes.

Flexures are mechanisms that include a series of rigid bodies connected by integral compliant elements to produce a geometrically well-defined motion upon application of a force. The present inventors recognized that flexures offer many potential benefits: they are relatively simple and inexpensive to manufacture and assemble; unless fatigue cracks develop, the flexures undergo no irreversible deformation (elastic deformation) and are therefore wear free; complete mechanisms may be produced from a single monolith; mechanical leverage is easily implemented; displacements are smooth and continuous even at the nanometer level of motion; failure mechanics such as fatigue and yield are well understood; they may be designed to be insensitive to thermal variation and mechanical disturbance (vibrations); symmetric designs may be inherently compensated and balanced; there is a linear relationship between applied force and displacement for small distortions; for elastic distortions, this linear relationship is independent of manufacturing tolerance, though the direction of motion will be less accurate as these tolerances are relaxed; and, flexures have atomic level of repeatability. Examples of such flexures/compliant mechanisms are disclosed in U.S. Pat. Nos. 7,093,827 and 7,270,319, both entitled Multiple Degree of Freedom Compliant Mechanism, to Martin L. Culpepper, and which patents are incorporated herein by reference for all purposes.

The present inventors further recognized that properly designed flexures allow relatively high accuracy motion control, even allowing errors due to manufacturing tolerances to be corrected. In comparison, more traditional mechanisms not based on flexures, such as the articulated linkages discussed hereinabove, tend to exhibit backlash, which may be difficult to control even in closed loop systems. This ultimately lowers their precision in comparison to flexure mechanisms. Flexures may thus be used to help achieve at least two goals: (1) providing a precise displacement upon application of a specific applied force, and (2) providing a precisely known force upon application of a specific applied displacement. (Flexures may also be used for motion amplification/deamplification, i.e. providing a precisely known displacement upon application of a specific applied displacement.)

As shown and described herein, the flexure coupling(s) of the present invention substantially eliminates unwanted parasitic motions without the need for a separate guide rail or the use of an articulated arm, while still maintaining relatively high stiffness or rigidity in desired directions. Embodiments of the present invention may substantially reduce cost, complexity, and wear, while improving instrument performance, robustness and manufacturability. The flexures effectively form high performance mechanical bearings which allow motion by the bending of a load element. Since they are constructed from a monolithic material (e.g., a single piece of metal), they have no internal moving parts, to provide excellent wear characteristics, and precise and repeatable ranges of motion.

In general, motion control requires two separate functional units: a force generating unit to actuate the motion and a bearing unit to constrain and guide the motion to the desired trajectory. Flexure bearings use elastic deformation of materials to generate degrees of freedom to allow some motions while minimizing others. The allowed motions are determined by the geometry cut into the material of the bearing.

For an oscillating microtome, as mentioned above, motion in the out of plane (z-direction as shown) may result in poor quality sectioning. The flexure stages shown and described herein may effectively minimize any such parasitic z-axis motions, providing a peak-to-peak amplitude on the order of 1 to 2 μm for a sample surface flatness of <1 μm at oscillation frequencies of 200 Hz or more.

Figure 1:
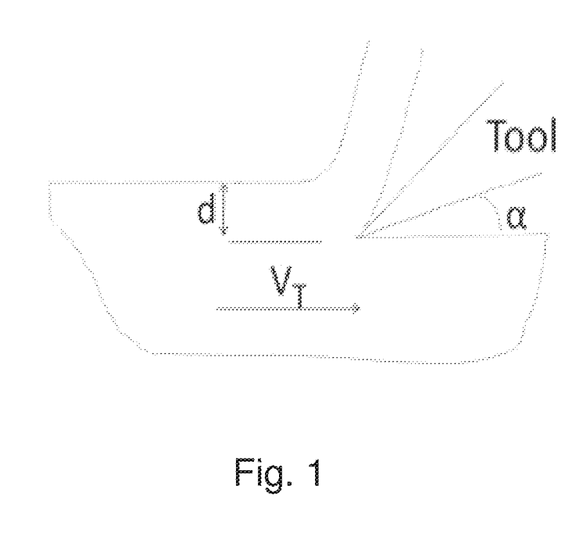
FIG. 1 is an elevational, schematic view of a sample being sectioned in accordance with aspects of the present invention.

Referring now the appended figures, exemplary embodiments of the present invention will be described in detail. Turning to FIG. 1, the volume of material removed per section(s) when using a microtome of the present invention, is given by the following Equation 1:

$$V_{Removed} = d * W * V_T \qquad \text{Eq. 1}$$

$V_T$ is the feed rate of the blade relative to the sample, d is the thickness of the section, W is the width of the tissue section sample, α is the tool (blade) cutting angle; F is the vibration (oscillation) frequency of the blade motion (along the x-axis in the coordinate system shown and described herein), and A is the amplitude of the blade motion.

As will be discussed in greater detail hereinbelow, the frequency and amplitude of the blade may be adjusted depending on the thickness of the tissue section, the feed rate, the tool angle, and the material properties of the tissue itself. In practice, good quality sections over a wide range of section thickness may be achieved by adjusting the cutting angle, feed rate and vibration frequency.

Turning now to FIG. 2, a microtome 20 (which may also be referred to as a microtome with a vibrating or oscillating blade) of the present invention uses a second flexure mechanism F2 in lieu of a conventional articulated linkage between an actuator (e.g., motor) 22 and the blade assembly 24. The flexure F2 is rigidly mounted to another motion guidance flexure mechanism shown as first flexure F1. The second flexure F2 is configured to decouple unwanted motions between the actuator and the blade assembly flexure F1. The flexure F2 may take any number of configurations that will be evident to those skilled in the art in view of the instant specification. Examples include, but are not limited to, folded beam, shape morphing designs, and bow flexures. Unlike the above-described mechanical linkages of the prior art, flexure F2 is stiff along the direction of the desired motion (i.e., along the x-axis as shown), and flexible in a direction orthogonal thereto (e.g., the y-direction as shown), without suffering from buckling.

As also shown, actuator 22 provides the oscillatory force to drive the blade. Particular embodiments of the actuator 22 include but are not limited to, a rotating electric motor with an offset cam or other eccentric, an eccentric drive, a solenoid, and an electromagnet.

The flexure F1 guides the motion of the blade, typically an oscillatory motion along the x-axis. Particular embodiments of F1 guide the blade along an arcuate path as this has been shown to improve section quality in some applications.

Thus, in particular embodiments, flexure F2 is linearly and rotationally constrained along x, z, and θy, and is not constrained along y, θx, or θz. Flexure F1, to which the blade assembly is rigidly attached, is constrained along y, z, θx, θy, and θz, and is not constrained along x.

The aforementioned stiffness in the x-direction, and compliance in other directions, enables flexure F2 to help maintain parasitic motion, particularly force transmitted in the out of plane (z-axis) direction as a relatively small fraction of the motion and force along the x-axis. Typical ratios exhibited by the embodiments shown and described herein may be on the order 0.0001 or one part in 10,000. It is also noted that the compliance of flexure F2 may compensate for various misalignments, such as may be due to imprecise mounting of the actuator 22. That is, position and angle errors along one or more of its unconstrained degrees of freedom may be effectively decoupled by its compliance, while transmitting motion in the x-direction. This helps to facilitate relatively precise motion control.

These configurations provide for a relatively small overall system footprint, and tend to be superior to prior art approaches, e.g., in terms of size, performance and/or cost. This use of flexure F2 also provides flexibility to tailor the dynamics of the driving force to the oscillating blade.

Turning now to FIGS. 3A and 3B, a representative embodiment of a microtome of the present invention is shown as 20'. The blade holder assembly 24' is connected to a mounting platform (ground) 28 through a flexure arm F1' which allows motion along the x-axis. The blade holder assembly 24' is actuated via flexure F2' connected to an actuator 22' in the form of an electric (e.g., DC) motor (e.g., a Faulhaber 3863H012C, by Faulhaber). The motor 22' is connected to the flexure F2' by use of an eccentric 30, e.g., in the form off center cam as shown. Cams with different offsets may be used to adjust the amplitude of the oscillatory motion. As described above, the flexure linkage F2' transforms the rotary motion of the DC motor 22' to a harmonic linear motion with a frequency corresponding to the rotational speed of the motor 22'. As also discussed above, the flexure linkage F2' minimize any forces transmitted to the blade holder assembly 24' which are not co-linear with the desired linear motion (e.g., along the x-axis) of the blade.

In the particular embodiment shown, flexure F2' includes a series of flexible beams 29 spaced from one another in the cut direction. In the example shown, flexure F2' is provided with a relatively high resistance to buckling by use of an aspect ratio (i.e., length L to width W, FIG. 3A) which is low relative to that of a conventional leaf spring. This use of parallel beams, with one or more connectors 31 therebetween, provides the overall flexure F2' with both relatively high stiffness in the x-direction to prevent buckling, while still providing relatively high flexibility in a direction (e.g., y-direction) orthogonal thereto. It should also be noted that these aspects enable flexure F2' (and F2", FIG. 6) to move in a substantially frictionless manner during oscillation. This contrasts with conventional articulated linkages and leaf spring approaches which rely on engagement with a substantially stationary guide rails in order to maintain the desired motion.

As shown, beams 29 extend from the one end portion towards the other end portion of flexure F2', and in the particular embodiment shown, extend substantially parallel to one another. In this regard, it should be noted that beams that are bowed, curved, and/or with varying cross-sectional area when at rest, such as the alternate beams shown in phantom at 29' in FIG. 3A, would still be considered to be substantially parallel with one another. In this regard, as mentioned above, bowed beams, or beams having substantially any other desired shaped, may be used without departing from the scope of the present invention.

In particular embodiments, the flexible beams 29, 29', etc., are configured to extend in the transverse direction (e.g., x-direction as shown) at some point (e.g., the midpoint) of the oscillation cycle as shown. Moreover, it should be recognized that during the oscillation, the one end portion of the second flexure F2' connected to the first flexure F1', is configured to move in the transverse (e.g., x) direction, while being substantially prevented from moving in the cut (e.g., y) direction, while the other end portion connected to actuator 22', is configured to move in both the transverse and cut directions.

As also shown, particular ones of the beams 29, 29' are connected to one another with connectors 31 disposed at spaced locations along the length of flexure F2'. In particular embodiments, at least one connector 31 is disposed within approximately the middle 50 percent (%) of the length L of the flexure F2'.

The frequency of the cutting motion may be set by adjusting the speed of the motor 22'. The amplitude of the motion may be specified by adjusting the offset of the cam 30, as discussed above, e.g., either by replacing the cam 30 with one having a different offset, or by employing a cam having an adjustable offset, as will be familiar to those skilled in the art.

A blade 32 may be fastened to the blade holder assembly 24' in any convenient manner, such as by clamping using a micro flexure. The blade angle α(FIG. 1A) may be manually adjusted by rotating the blade holder and locking it to the blade holder assembly, as will be discussed in greater detail hereinbelow. As a non-limiting example, the blade 32 is a 2.5"×0.3" carbon steel blade of the type commonly used in histology. The F1' and F2' flexures may be manufactured out of, for example, Aluminum (e.g., Aluminum 7075 or 6061), titanium, spring steel, and/or silicon. Electrical discharge machining or a water jet may be used to manufacture any one or more (or all) of flexure F1', flexure F2', and mounting platform 28, from a single monolithic piece of material as shown in FIG. 3B. In this regard, in general, any material having a relatively high yield strength to elastic modulus ratio may be used.

Figure 4A:
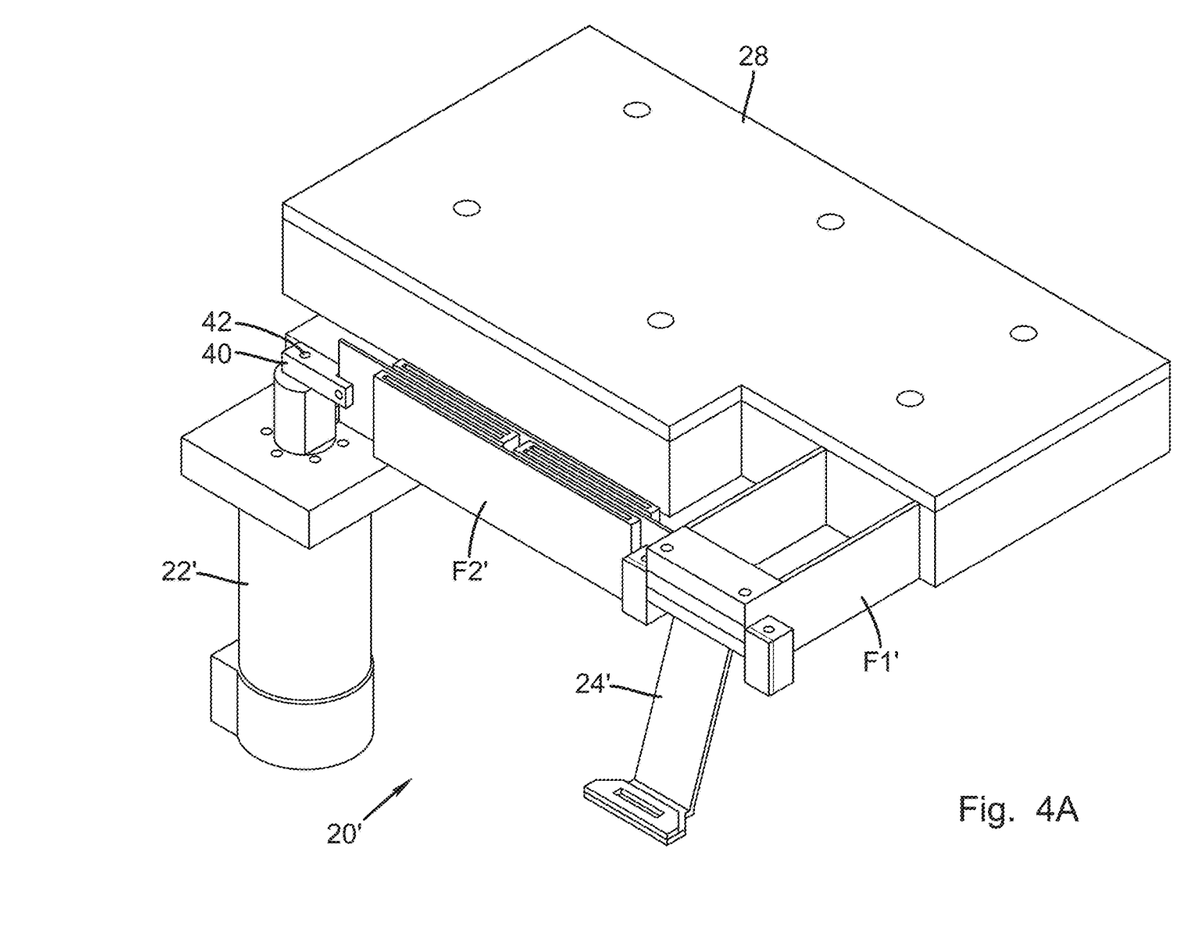
FIG. 4A is a perspective view of the embodiment of FIG. 3A.
Figure 4B:
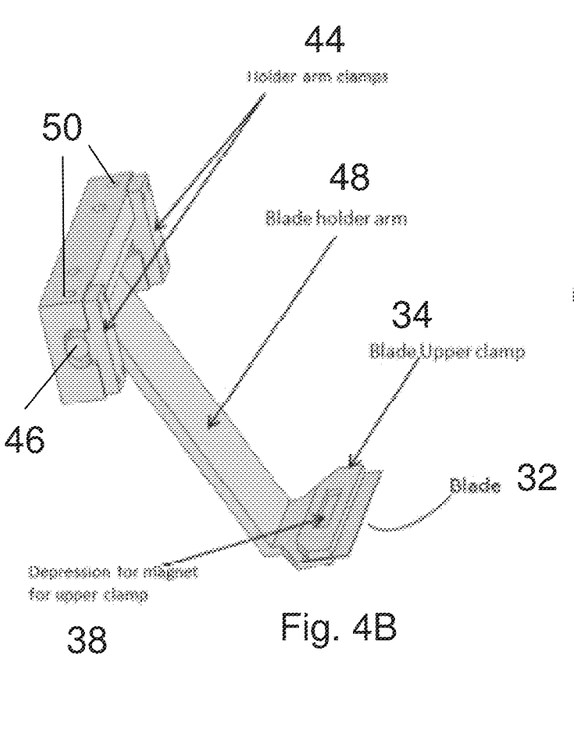
FIGS. 4B and 4C are top and bottom perspective views of elements of the embodiment of FIG. 4A.
Figure 4C:
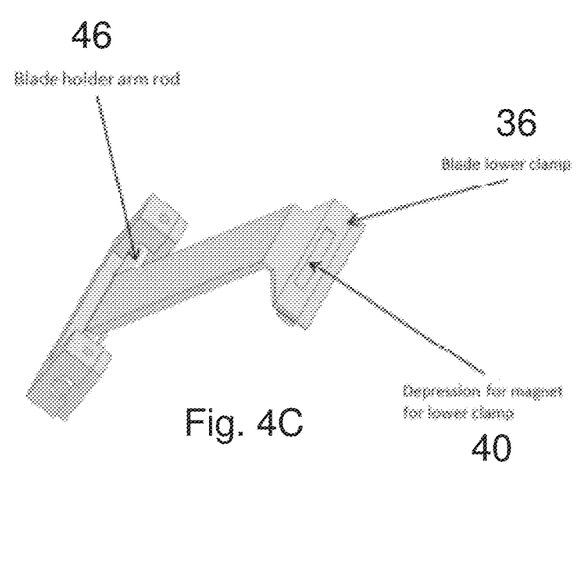

With reference now to FIGS. 4A-4C, aspects of microtome 20' will be described in greater detail. Turning to FIG. 4A, microtome 20' is shown with actuator (motor) 22' and blade holder 24' disposed in operational engagement with flexure F1'. Flexure F2' is connected at one end to flexure F1', and at the other end to motor 22'. The connection and relative orientation of flexure F2' with motor 22' may be accomplished in any convenient manner. For example, a connector 40 may be used, which connects via set screw to the flexure F2' at one end, while rotatably engaging a dowel 42 extending from offset cam 30 (FIG. 3A) at the other end. The offset cam is mounted to the shaft of the motor 22'.

The blade holder assembly 24' has a number of unique features, which will now be described with reference to FIGS. 4B-4D.

Turning now to FIGS. 4B and 4C, embodiments of the blade holder may include a blade clamping mechanism including an upper clamp 34 and a lower clamp 36. Small magnets (not shown), e.g. neodymium magnets, may be receivably disposed within receptacles 38 and 40 of clamps 34 and 36, respectively, to provide a compressive force capable of securely fastening the blade 32 to the blade holder assembly 24'. The upper clamp 34 may also be provided with a curved surface (not shown) configured to allow the tissue section to slide easily on the blade holder while it is being sectioned as shown in FIG. 1A.

As also shown, the blade holder 24' may be attached in a variable manner to flexure F1' to facilitate changing angle α(FIG. 1) that the blade 32 makes with respect to the tissue to be sampled. In the embodiment shown, angle α may be adjusted by loosening the holder arm clamps 44 to release the arm rod 46 to permit the blade holder arm 48 to be pivoted thereabout. Once set at the desired angle, the blade holder arm 48 may be secured in place by tightening the holder arm clamps 44.

In addition, provision may be included to adjust the blade 32 in the z-direction, to permit precise level adjustment of the blade 32 relative to the tissue being cut. For example, such adjustment may be provided set screws 50 disposed to adjust the position along the z-axis of the blade holder arm rods 46 prior to being secured by claims 44.

Thus, as shown and described, blade holder 24' is relatively lightweight, to enable increased frequency and amplitude of the blade motion relative to many prior art approaches. The magnetic clamping system provides for a relatively low mass to force ratio. The magnetic clamping mechanism is also easy to use and does not require the use of tools to remove and replace the blade 32. It offers high reproducibility and the entire assembly may be easily manufactured, such as by using conventional 3D printing technology. This tends to reduce cost and increase design flexibility.

Figure 4D:
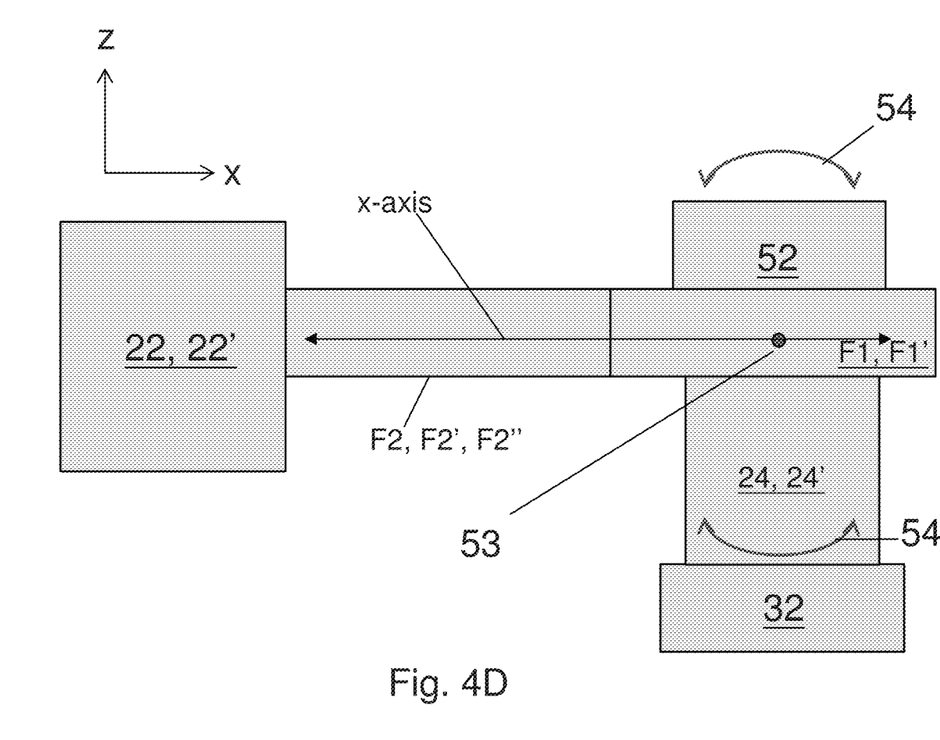
FIG. 4D is a schematic elevational view illustrating aspects of the embodiments of FIGS. 2-4C.
Figure 6:
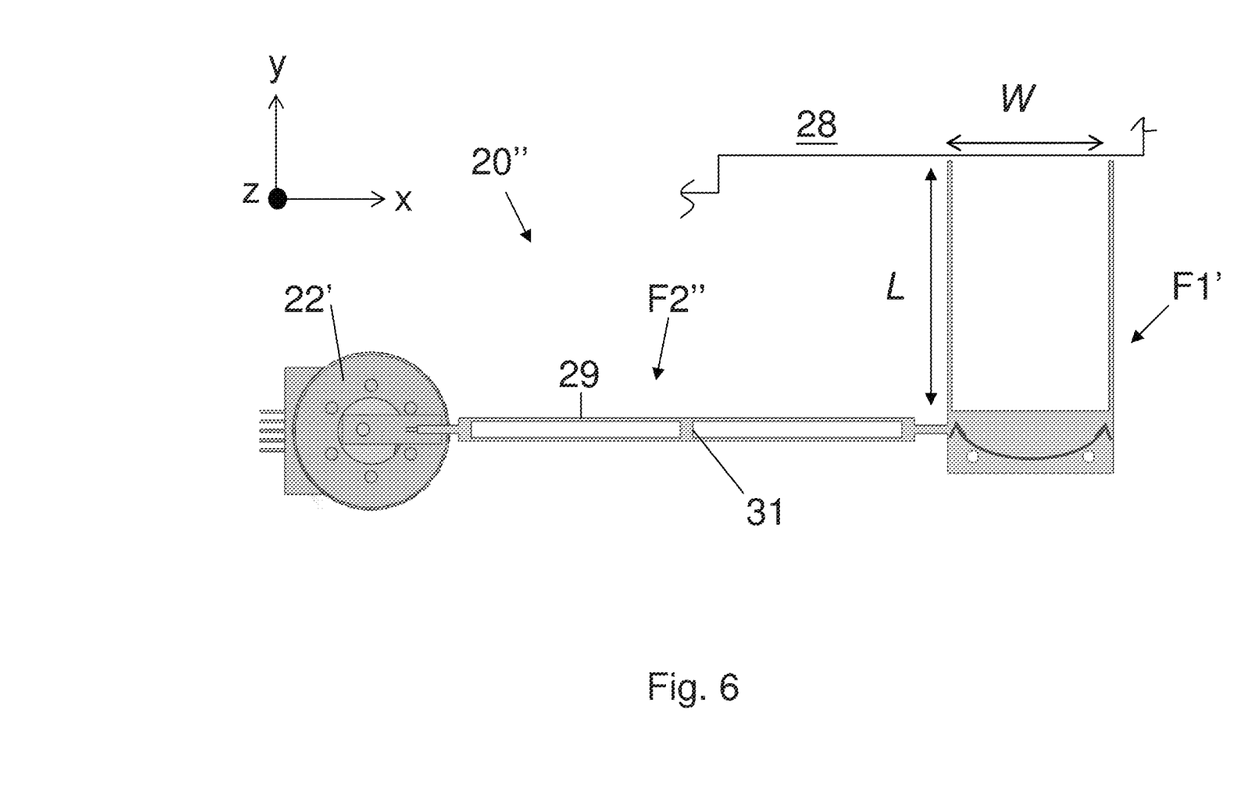
FIG. 6 is a schematic plan view of an alternate embodiment of the present invention.

Turning now to FIG. 4D, this lightweight approach also enables the center of stiffness of the blade holder 24' (with respect to motion in the θy direction) to be located relatively close to the x-axis, which in the embodiments shown, passes through the geometric center of flexure F2' (and F2", FIG. 6). Indeed, in some embodiments, a mass 52 may be disposed on the blade holder 24' on a side opposite that of the blade 32, which is sized to bring the center of stiffness to the x-axis as shown at 53. This approach helps to reduce, if not substantially eliminate, any parasitic swing motion (shown at 54) of the blade holder 24' about the y-axis, which would tend to generate parasitic error motion in the z-direction during oscillation. It should also be recognized that any θx error motion (i.e., rotation about the x-axis), which would also generate parasitic error motion along the z-axis, is also reduced by the relatively low mass of the blade holder 24' as shown and described herein. These features of blade holder 24', in combination with the use of flexures F1, F1' and F2, F2', F2" as shown and described herein, have been shown to reduce any parasitic z-motion of the blade holder 24' to between 0.5 and 1.0 micron.

Figure 5:
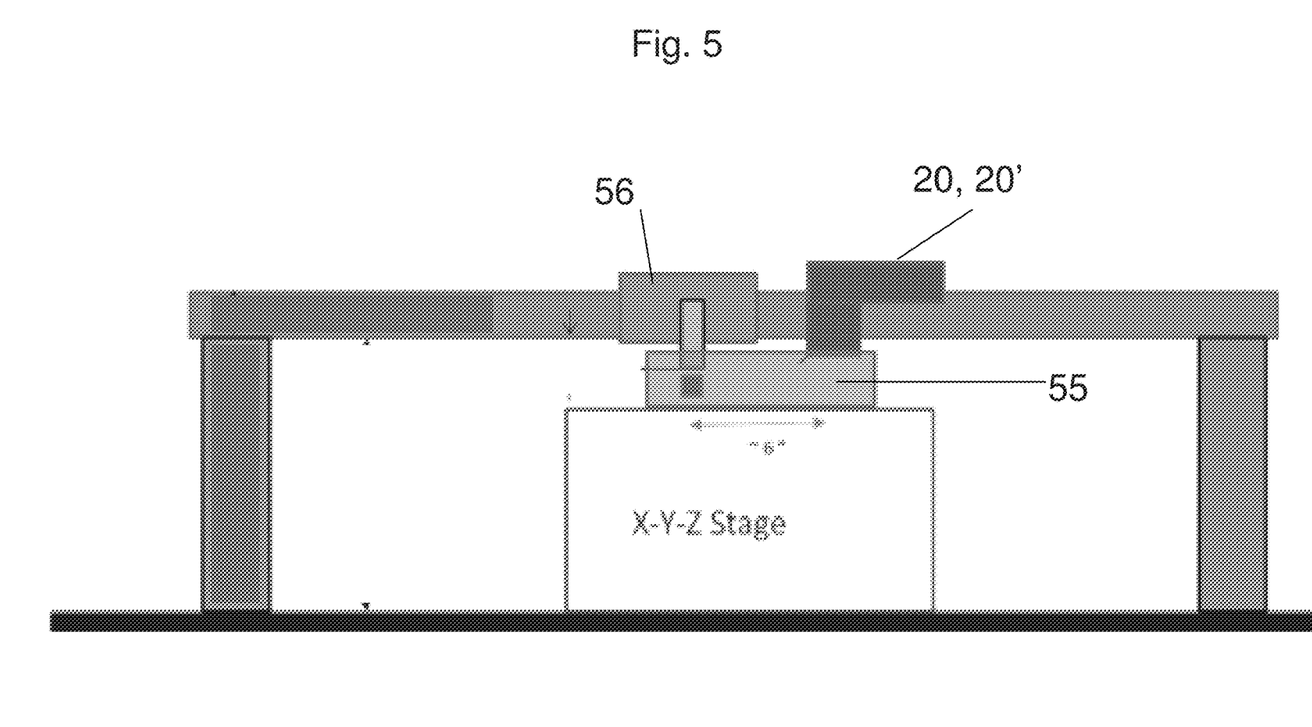
FIG. 5 is a schematic elevational view of a representative application incorporating the embodiments of FIGS. 2-4D.

Turning now to FIG. 5, as shown schematically, microtome 20, 20', etc., may be incorporated within an imaging system to effect both sectioning and imaging of a sample. For example, in an exemplary embodiment, the sample may be placed within a bath (e.g., water bath) 55 which may be moved along the cutting axis (e.g., along the x-axis, FIG. 2) relative to microtome 20, 20', etc., for sectioning, and an imaging device such as a microscope 56, for imaging. Substantially any microscope or other imaging device including conventional CCD and/or laser scanning PMT (Photomultiplier tube)—based devices may be used. In this regard, examples of both imaging (i.e., microscope) systems and methodologies with which the microtomes 20, 20', etc., of the instant invention may be used, are disclosed in U.S.

Pat. No. 7,372,985, entitled Systems and Methods for Volumetric Tissue Scanning Microscopy, which patent is fully incorporated herein for all purposes.

Turning now to FIG. 6, an alternate embodiment of the present invention is substantially similar to the embodiment shown and described in FIGS. 3A-4C, but for the use of an alternative second flexure F2". This flexure F2" uses dual, parallel beams 29 with a single connector 31 disposed within the middle 50 percent of the length of the flexure F2", e.g., at the midpoint of the longitudinal dimension of the flexure F2". This particular embodiment uses only a single connector 31 within this middle 50 percent, though a plurality of connectors disposed in spaced relation along the beams 29 may also be used, if desired to provide additional resistance to buckling. This construction provides a smaller footprint than flexure F2', and a less complex dual-beam construction, which tends to lower the moving mass and simplify construction for comparatively higher frequency operation and lower parasitic motion in many applications.

Referring back to FIG. 2, flexures F2, F2', F2", etc., have been shown to provide a high ratio of x-direction stiffness ($K_{X2}$) to y-direction stiffness ($K_{Y2}$), for efficient error motion decoupling. Examples of flexure F2" in particular, fabricated from aluminum, have been shown to provide a ratio $K_{X2}/K_{Y2}$ of at least approximately 500, and in particular embodiments, more than 2500.

It is noted that microtome 20 (and 20', 20", etc.) will have a resonance frequency that may vary depending upon the particular parameters (e.g., stiffness) of the flexures F1, F1', and F2, F2', F2", etc., used in any particular embodiment. In general, the stiffer the flexures (e.g., in both the x and y directions), the higher the resonance frequency of the microtome system. Embodiments of the present invention may be provided with a resonance frequency that is at least about 2 to 4 times the highest desired operational speed of the microtome, to ensure smooth operation of the microtome.

It should be recognized that using a flexure that is excessively compliant in the y direction (i.e., has a very low $K_{Y2}$) may make it easy to achieve the relatively high ratio $K_{X2}/K_{Y2}$ as indicated above. However, such a low $K_{Y2}$ may provide the microtome with a resonance frequency that will be too low for some applications. Thus, the skilled artisan will recognize, in light of the teachings hereof, that embodiments of the present invention may be provided with a balance between the ratio $K_{X2}/K_{Y2}$ and the resonance frequency of the system, to achieve desired performance at particular operational speeds.

Particular examples of microtome 20, 20', 20", have a resonance frequency of at least 500 Hz. Similarly, in many applications it may be desirable for embodiments of the invention to have an out-of-plane (z-axis) mode shape at a frequency that is at least about 4 to 8 times the highest desired operational speed of the microtome, to help prevent the occurrence of unwanted parasitic motion. Particular examples of microtome 20, 20', 20", etc., have been shown to have a z-axis mode shape frequency of at least 700 Hz.

As also shown, flexure F1, F1' has essentially the opposite ratio as that of flexures F2' and F2", i.e., flexure F1' has a relatively high ratio of y-direction stiffness ($K_{Y1}$), to x-direction stiffness ($K_{X1}$). It is also noted that while flexure F1, F1', provides for the desired x-direction oscillation, the instant inventors have also discovered that a slightly arcuate path, such as shown in FIG. 6, tends to improve the surface quality of the section. Thus, particular embodiments of flexure F1, F1' may be provided with a ratio of length (L) to width (W) within the range of about 1.5 to 3, with a length L within the range of about 5 to 12 cm.

Referring now to Table 1 below, the microtomes of the present invention, including flexures F2', F2", in combination with the low mass blade holder 24', have been shown to provide operational speeds of above 200 Hz with parasitic z-motion of less than 2 microns, with particular embodiments exhibiting operational speeds of up to 300 Hz with less than 1 micron of parasitic z-axis motion.

TABLE 1

| Inventive Microtome Example | |
|---|---|
| Microtome Specifications | Tissue: Rabbit myocardial, mouse brain |
| Feed rate | 0.1-10 mm/s |
| Vibration Frequency | 15-400 Hz |
| Vibration Amplitude | 0.1-2 mm |
| Section Thickness | 10-2000 µm |
| Blade angle | 5-30 degrees |
| Parasitic z-motion | <1.5-3 µm |
| Cutting Characteristics | |
| Surface Quality | <2 µm RMS |

The flexures of this invention may be fabricated from substantially any material. Prototypes have been fabricated using metallic materials, such as aluminum, using an abrasive water jet cutting tool. Metallic compliant mechanisms may be advantageous in that they may provide for both elastic and plastic deformation of the mechanism's components. It is further envisioned that the compliant mechanisms of this invention may be fabricated from other materials, such as silicon or doped silicon wafers, using a technique such as deep reactive ion etching (DRIE).

Having described various embodiments of the apparatus of the present invention, a representative method of operation will now be described. For example, a method of treating a sample includes using any of the microtomes 20, 20', 20" to oscillate the microtome blade in a direction transverse to a direction of advancing a cut; and moving the sample in the cut direction, into operative engagement with the oscillating microtome blade to remove a section from the sample. Optionally, the sample may be moved into operative engagement with an imaging device, such as a microscope, which is then used to image the sample. In particular embodiments, the image may be captured by the imaging device and stored for later reference.

The artisan of ordinary skill will readily recognize that there are many variable shapes and configurations for the various portions of the flexures that may be used to alter the various operational parameters of embodiments of this invention. It should be further understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A microtome apparatus comprising:
   a microtome blade configured to oscillate in a direction transverse to a direction of advancing a cut;

a first flexure configured to support and guide the blade, said first flexure configured to be compliant in the transverse direction while being stiff in the cut direction;

a second flexure operatively engaged at one end portion thereof with the first flexure, the second flexure configured for being stiff in the transverse direction while being compliant in the cut direction;

a rotating actuator;

an eccentric driven by the actuator;

the second flexure being rotatably engaged at another end portion thereof with the eccentric, wherein operation of the actuator serves to oscillate the blade in the transverse direction while effectively isolating non-transverse motion from the blade; and the second flexure being configured to move independently of any stationary objects during said oscillation.

2. The apparatus of claim 1, wherein the first flexure is configured for being stiff in a direction (out of plane direction) orthogonal to both the cut and transverse directions.

3. The apparatus of claim 2, wherein the second flexure is configured for being stiff in the out of plane direction.

4. The apparatus of claim 1, wherein the blade is configured for oscillation at a frequency within a range of 15 to at least 400 Hz, an amplitude of movement in the transverse direction within a range of 0.1 to at least 2 mm, and an amplitude of parasitic movement in the out of plane direction of no more than 1.0 to 3.0 micron.

5. The apparatus of claim 1, wherein the second flexure is configured to move in a substantially frictionless manner during said oscillation.

6. The apparatus of claim 5, wherein the second flexure is monolithic.

7. The apparatus of claim 6, wherein the second flexure comprises a plurality of flexible beams spaced from one another in the cut direction.

8. The apparatus of claim 7, wherein the plurality of flexible beams extend from the one end portion towards the other end portion.

9. The apparatus of claim 8, wherein the plurality of flexible beams extend substantially parallel to one another.

10. The apparatus of claim 8, wherein the plurality of flexible beams are configured to extend in the transverse direction during a portion of said oscillation.

11. The apparatus of claim 7, wherein during said oscillation, the one end portion is configured to move in the transverse direction, while being substantially prevented from moving in the cut direction, while the other end portion is configured to move in both the transverse and cut directions.

12. The apparatus of claim 7, wherein the second flexure further comprises at least one connector disposed to join individual ones of said flexible beams to one another, said at least one connector disposed in spaced relation from said end portions.

13. The apparatus of claim 12, wherein said at least one connector is disposed within the middle 50 percent of the length L of the second flexure.

14. The apparatus of claim 1, wherein the second flexure has a ratio $K_{x2}/K_{y2}$ of coefficient of stiffness in the transverse direction ($K_{x2}$) to coefficient of stiffness in the cut direction ($K_{y2}$) of at least about 500 to 2500.

15. The apparatus of claim 14, wherein the microtome is configured to have a resonance frequency on the range of 2 to 4 times the speed of oscillation in the transverse direction.

16. The apparatus of claim 14, wherein the microtome is configured to have a resonance frequency of at least 500 Hz.

17. The apparatus of claim 3, wherein the microtome is configured to have an out-of-plane mode shape frequency in the range of 4 to 8 times the speed of oscillation in the transverse direction.

18. The apparatus of claim 17, wherein the microtome is configured to have an out-of-plane mode shape frequency of at least 700 Hz.

19. The apparatus of claim 1, wherein the first flexure has ratio of length (L) in the cut direction to width (W) in the transverse direction, within the range of about 1.5 to 3.

20. The apparatus of claim 1, wherein at least one of the first and second flexures comprise a monolithic structure.

21. The apparatus of claim 20, wherein said first and second flexures each comprise a monolithic structure.

22. The apparatus of claim 21, wherein said first and second flexures comprise a single monolith.

23. The apparatus of claim 1, wherein the blade is disposed on a blade holder, said blade holder extending in a cantilevered manner from the first flexure, the blade holder having a center of rotation about an axis parallel to the cut direction, said center of rotation being disposed on a transverse axis passing through said first and second flexures.

24. The apparatus of claim 23, wherein said blade holder comprises a magnetic mount configured to retain the blade thereon.

25. The apparatus of claim 1 wherein at least one of said first and second flexures is fabricated from an aluminum alloy.

26. The apparatus of claim 1 wherein at least one of said first and second flexures is fabricated from at least one of aluminum, titanium, spring steel, or silicon.

27. A tissue scanning imaging apparatus comprising:
the microtome apparatus of claim 1;
an imaging device; and
a stage configured to selectively advance a specimen sample into operative engagement with both the microtome apparatus and the imaging device.

28. A method of treating a sample, said method comprising, with the microtome apparatus of claim 1:
(a) oscillating the microtome blade in a direction transverse to a direction of advancing a cut; and
(b) moving the sample in the cut direction, into operative engagement with the oscillating microtome blade to remove a section from the sample.

29. The method of claim 28, further comprising:
(c) moving the sample into operative engagement with an imaging device; and
(d) imaging the sample.

* * * * *